United States Patent
Gabura et al.

(10) Patent No.: US 7,244,937 B1
(45) Date of Patent: Jul. 17, 2007

(54) OPTICAL MEASUREMENT APPARATUS WITH LASER LIGHT SOURCE

(75) Inventors: Andrew J. Gabura, Penetanguishene (CA); Blaise R. Robitaille, Penetanguishene (CA); Roger W. Ball, Midland (CA)

(73) Assignee: Raytheon Company, Lexington, MA (US)

( * ) Notice: Subject to any disclaimer, the term of this patent is extended or adjusted under 35 U.S.C. 154(b) by 710 days.

(21) Appl. No.: 10/271,956

(22) Filed: Oct. 15, 2002

(51) Int. Cl.
*G01J 5/08* (2006.01)
(52) U.S. Cl. .................. 250/341.2; 250/351; 356/418
(58) Field of Classification Search ............ 250/341.2, 250/351; 356/418
See application file for complete search history.

(56) References Cited

U.S. PATENT DOCUMENTS

| | | | | |
|---|---|---|---|---|
| 4,669,873 A | * | 6/1987 | Wirz | 356/73 |
| 4,671,613 A | * | 6/1987 | Buhrer | 359/495 |
| 5,347,604 A | * | 9/1994 | Go et al. | 385/92 |
| 5,455,673 A | * | 10/1995 | Alsmeyer et al. | 356/301 |
| 5,526,121 A | * | 6/1996 | Sandifer et al. | 356/418 |

OTHER PUBLICATIONS

Anon. "OMS 3000", Leybold Systems, 1998, pp. 1-1 to 1-5; pp. 2-1 to 2-9; p. 7-1.

* cited by examiner

*Primary Examiner*—David Porta
*Assistant Examiner*—Shun Lee
(74) *Attorney, Agent, or Firm*—Rene Grossman, Esq.; H. Saint Julian; Leonard Alkov

(57) ABSTRACT

An optical measurement apparatus operable with a test specimen has a light source with a laser having an output beam, and a beam splitter that splits the output beam of the laser into a first split beam and a second split beam. A test specimen holder holds the test specimen therein. A first optical fiber receives the first split beam and directs the first split beam against the test specimen in the test specimen holder. The apparatus further includes an instrumentation module. A second optical fiber receives the second split beam and conducts the second split beam to the instrumentation module. A third optical fiber receives signal light from the test specimen in the test specimen holder and conducts the signal light to the instrumentation module.

20 Claims, 3 Drawing Sheets

OPTICAL MEASUREMENT APPARATUS WITH LASER LIGHT SOURCE

This invention relates to optical measurement apparatus and, more particularly, to an optical measurement apparatus with a high intensity laser light source.

BACKGROUND OF THE INVENTION

Monolayer and multilayered thin films deposited on a substrate are used in a number of optical and other applications. The layers of such thin films are usually less than 1 micrometer, and sometimes much less than 1 micrometer, in thickness. They must be of precisely deposited thicknesses to be useful.

The thin films are typically deposited by a vacuum deposition process such as electron beam deposition. A source of the deposited material and the target substrate are placed into a vacuum chamber, and the source is operated to deposit the required material to the required thickness. There are typically multiple sources as required for the multiple layers.

The operation of the sources is calibrated so that the thickness of the deposited layers is reasonably well known. However, variations in the deposition rate usually are present so that the thicknesses of the layers cannot be known with sufficient precision, just from the deposition parameters.

Monitoring devices are therefore employed to measure the thickness of the thin film as it is gradually deposited, and to halt the deposition when the required thickness is reached. The monitoring device may measure directly on the test specimen of interest, or on a surrogate test specimen present solely for the purpose of providing the thickness measurement.

Monitoring devices typically operate by optical reflection of a light beam from, or optical transmission of a light beam through, the thin film being measured. In one such instrument, the Leybold OMS 3000, the light from a broadband tungsten halogen light source is split into dual beams. The two beams are each directed through an optical chopper. One of the chopped light beams is reflected from or transmitted through the thin film being measured, and then provided to a monochromator. The other chopped light beam serves as a reference and is provided to the monochromator. The intensity of the reflected or transmitted beam, after normalization for the reference light intensity, serves as a measure of the thickness of the thin film being deposited.

This apparatus is operable, but the present inventors have observed that it suffers from poor performance in its signal-to-noise ratio and an insufficient resolution bandwidth. The result is that its performance is limited in its function of providing a real-time measurement of the thickness of the thin film being deposited. There is therefore a need for an improved thickness measurement apparatus for monitoring the thin films as they are being deposited. The present invention fulfills this need, and further provides related advantages.

SUMMARY OF THE INVENTION

The present invention provides an optical measurement apparatus that is useful in measuring the thicknesses of thin films. It may be used in conjunction with a thin-film deposition apparatus to measure the thin films as they are deposited, so that the deposition apparatus may be controlled. It may instead be used in separate measurements of thin films used for optical and other applications. The efficiency of the apparatus is significantly improved as compared with existing measurement devices, with corresponding improvements in the signal-to-noise ratio and the resolution bandwidth.

In accordance with the invention, an optical measurement apparatus operable with a test specimen comprises a light source, itself comprising a laser having an output beam, and a beam splitter that splits the output beam of the laser into a first split beam and a second split beam. A test specimen holder holds the test specimen therein. A first optical fiber receives the first split beam and directs the first split beam against the test specimen in the test specimen holder. A second optical fiber receives the second split beam and conducts the second split beam to an instrumentation module. A third optical fiber receives a light measurement signal from the test specimen in the test specimen holder and conducts the light measurement signal to the instrumentation module.

The laser may be of any type, but is preferably an infrared laser. The light source desirably includes a light collimator that directs the output beam to the beam splitter, and a source optical fiber that conducts the output beam from the laser to the light collimator. The output beam is preferably substantially cylindrically symmetric in cross section and desirably has a diameter of at least about 2 millimeters when it is incident upon the beam splitter. The beam splitter is preferably a prism. The light source further preferably includes a first light chopper positioned between the beam splitter and the first optical fiber, and a second light chopper positioned between the beam splitter and the second optical fiber. At least a portion of the light source is desirably mounted to a removable support.

In the deposition application of most interest, the test specimen holder is preferably mounted in a vacuum chamber that contains the test specimen holder. One or more deposition sources are also provided in the vacuum chamber.

Thus, in a more preferred embodiment, an optical measurement apparatus operable with a test specimen comprises a light source comprising a laser having an output beam, a beam-splitter prism that splits the output beam of the laser into a first split beam and a second split beam, a light collimator that directs the output beam to the beam splitter, and a source optical fiber that conducts the output beam from the laser to the light collimator. There is a removable support upon which at least a portion of the light source is mounted. A test specimen holder holds the test specimen therein, and is itself contained in a vacuum chamber. A first optical fiber receives the first split beam and directs the first split beam against the test specimen in the test specimen holder. An instrumentation module is provided to process and measure the light beams. A second optical fiber receives the second split beam and conducts the second split beam to the instrumentation module. A third optical fiber receives a light measurement signal from the test specimen in the test specimen holder and conducts the light measurement signal to the instrumentation module. Other compatible features as discussed herein may be used with this embodiment as well.

The present optical measurement apparatus provides a high-intensity, narrowband laser light source with excellent coupling efficiency into the optical fibers. Resolution of the measurement apparatus is improved as compared with other types of light sources. The result is more accurate monitoring of the thin film thickness and improved wavelength resolution in the apparatus.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
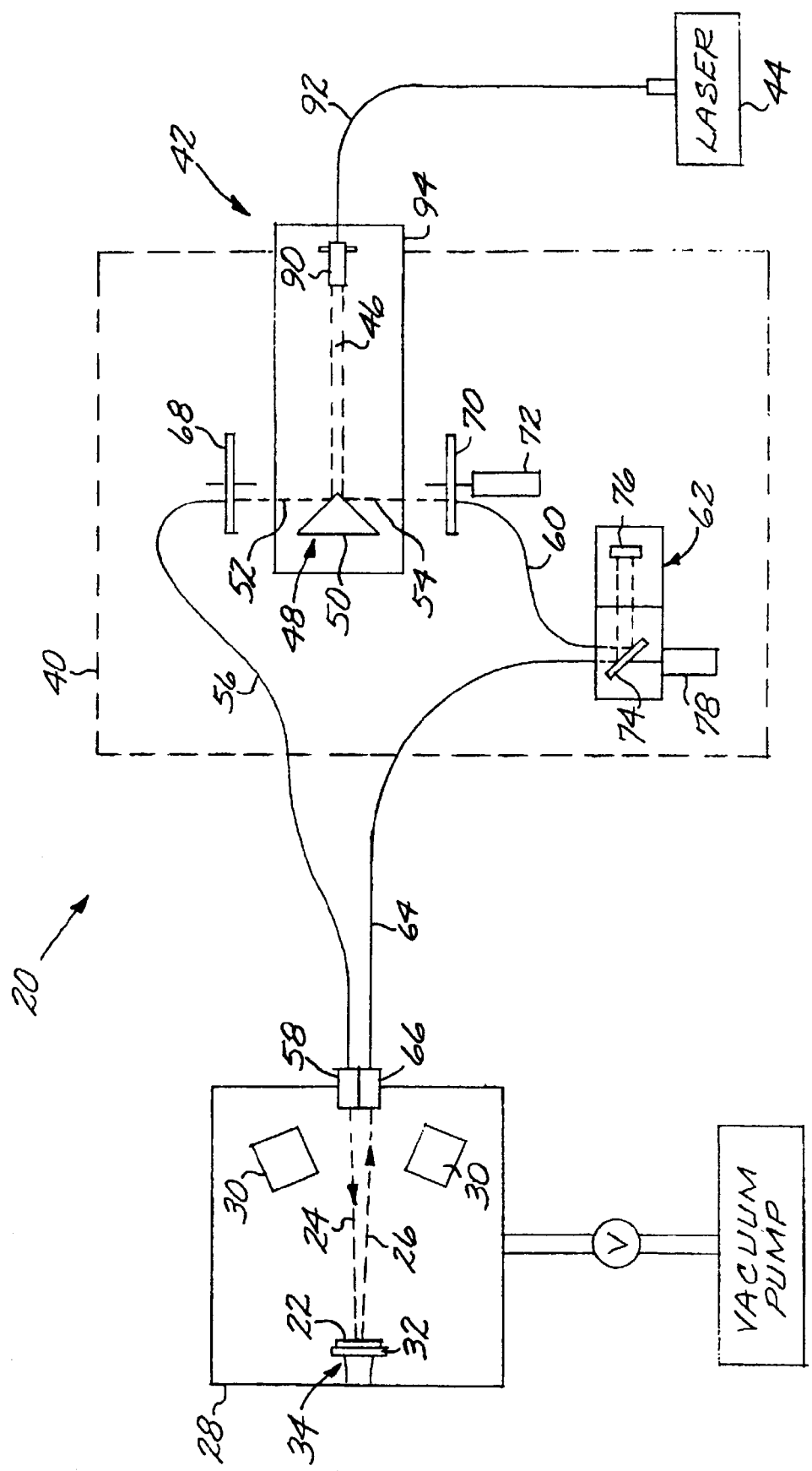
FIG. 1 is a schematic depiction of an optical measurement apparatus.

FIG. 1 depicts an optical measurement apparatus 20 operable with a test specimen 22, most preferably a thin-film test specimen. The optical measurement apparatus 20 optically measures physical characteristics of the test specimen 22, and therefore directs an incident light beam 24 onto the test specimen 22 and receives a reflected (as illustrated) or transmitted light measurement signal 26 from the test specimen 22. In a preferred application, the test specimen 22 is contained within a chamber 28, which is typically a vacuum chamber evacuated by a vacuum pump, but can also be a controlled-atmosphere chamber. In the illustrated case, the vacuum chamber 28 has deposition sources 30 therein to controllably deposit the test specimen 22 onto a substrate 32 supported from the wall of the vacuum chamber 28, thereby serving as a test specimen holder 34 for the optical measurement device 20. The test specimen 22 may have a single layer or, more commonly, a multilayer thin-film structure. The optical measurement apparatus 20 allows a continuous or semi-continuous measurement of the thickness of each layer of the thin-film test specimen 22 as it is deposited.

Figure 2:
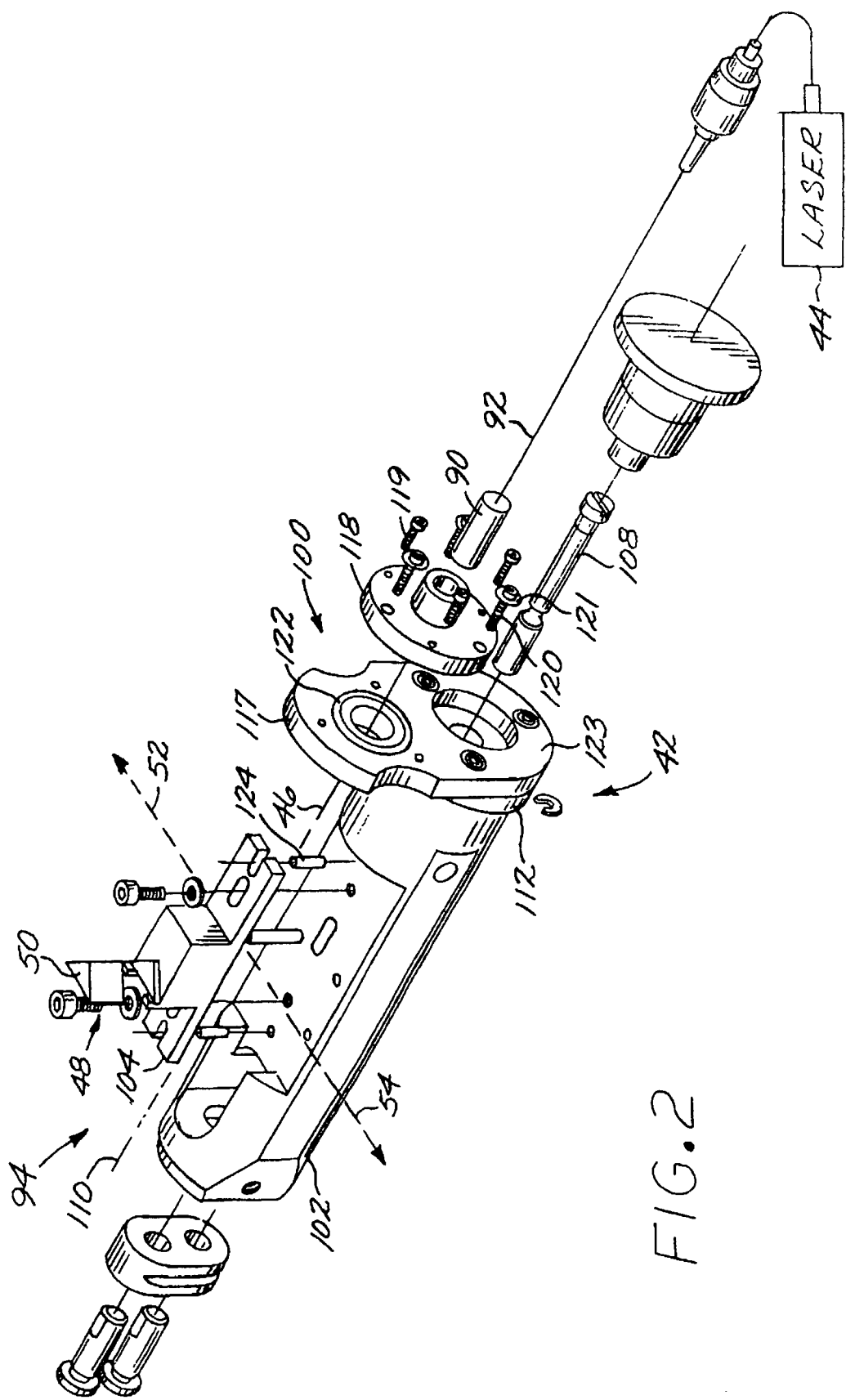
FIG. 2 is a partially exploded perspective view of the alignment mechanism for the removable support.
Figure 3:
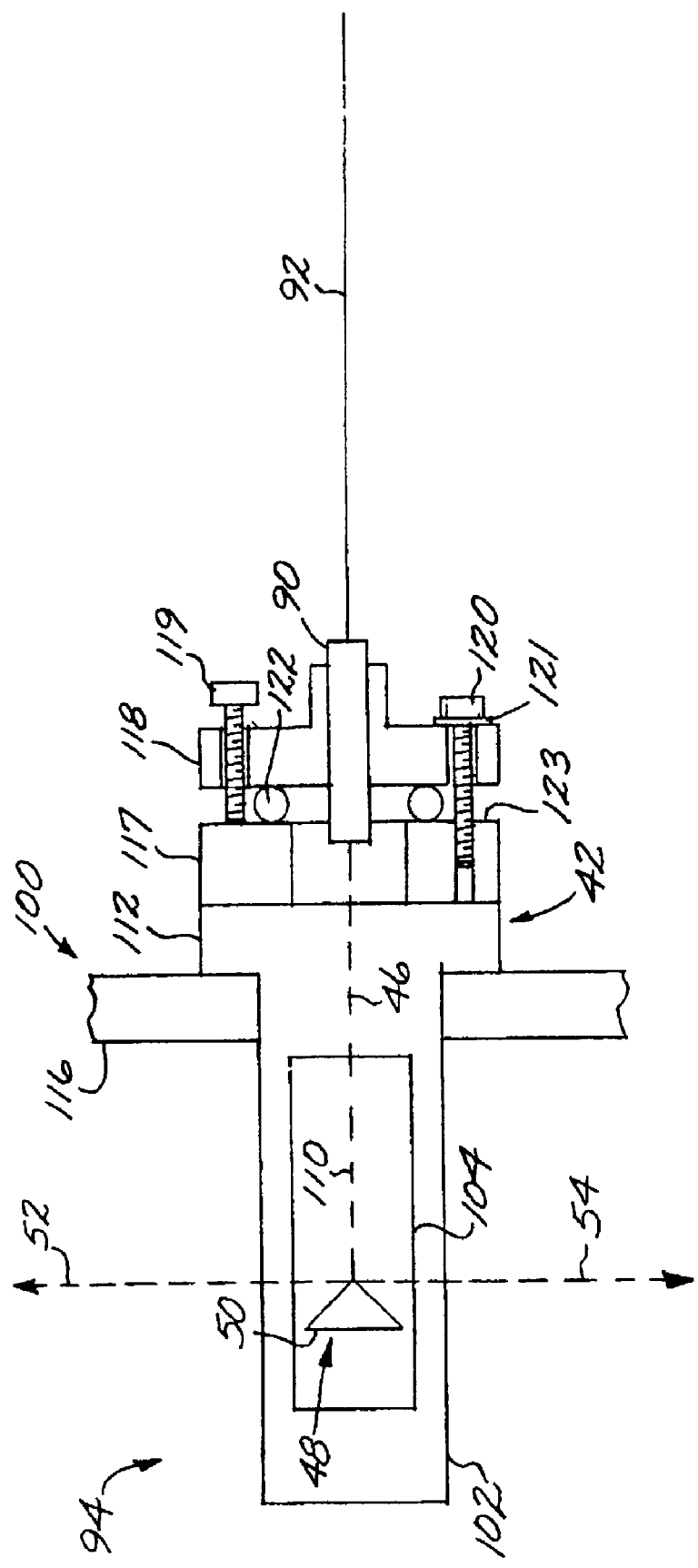
FIG. 3 is a schematic plan view of the alignment mechanism.

The optical measurement device 20 includes a housing 40 having a housing wall 116 that contains at least a portion of a light source 42 that is shown in FIG. 1 and in greater detail in FIGS. 2–3. The light source 42 includes a laser 44 having an output beam 46. The laser 44 desirably has a monochromatic output. In the preferred embodiment, the laser is an infrared laser operating at 1.55 micrometers output wavelength, but other lasers at other output wavelengths may be used. The output beam 46 is incident upon a beam splitter 48, which in this case is a prism 50 coated with an external mirror coating on the reflective faces, preferably gold for infrared reflection, that splits the output beam 46 of the laser 44 into a first split beam 52 and a second split beam 54.

In the preferred embodiment, the laser 44 is positioned remotely from the beam splitter 48. A light collimator 90 directs the output beam 46 through free space to the beam splitter 48. A source optical fiber 92 conducts the output beam 46 from the laser 44 to the light collimator 90. The output beam 46 projected from the light collimator 90 must be of sufficiently large diameter that it may be divided into the split beams 52 and 54 by the beam splitter 48. In a prototype, the projected output beam 46 has a diameter of at least about 2 millimeters, and preferably about 2.5 millimeters, when it is incident upon the beam splitter 48.

In the preferred approach, a portion of the light source 42, specifically the beam splitter 48 and the collimator 90, are mounted to a removable support 94. The removable support 94 and the optical elements mounted to it may be inserted into and removed from the housing 40 as a unit, so that the collimator 90 and beam splitter 48 may be readily aligned prior to insertion of the entire removable support 94 into the housing 40. The alignment is robust, as the alignment mechanisms are all incorporated into the removable support 94. The split beams are aligned with the receiving optical fiber (discussed subsequently) using the alignment mechanism. The removable support 94 may thereafter be removed from the apparatus and thereafter be re-installed without the need for further adjustment. The laser 44 is remotely located, and its light output, projected as the output beam 46, is conducted to the collimator 90 by the source optical fiber 92.

FIGS. 2–3 illustrate the alignment mechanism 100 of the removable support 94 in more detail. The removable support 94 includes a base 102 upon which a movable slide 104 is supported. Two vertical pins 124 extending upwardly from the base 102 fit into slots in the ends of the movable slide 104 and allow it to slide. A screw drive 108 that is affixed to the base 102 engages the slide 104 and drives it parallel to an axis 110 (that coincides with the output beam 46) to align the prism 50 and thence the split beams 52 and 54 (with the respective optical fibers 56 and 60, to be discussed subsequently). An accessory base flange 117 is rigidly mounted to a flange 112, which is part of the base 102. The collimator 90 is rigidly attached to a collimator holder flange 118. Three long screws 120 with washers 121 pass through oversize holes in the collimator holder flange 118 and thread into the accessory base flange 117. An "O" ring 122 positioned between the two flanges 117 and 118 provides resilient support while allowing sufficient movement to adjust the collimator output beam 46. Three short screws 119 thread into the collimator holder flange 118 and contact the accessory base flange surface 123, locking the alignment into place. In summary, the alignment of the prism 50 and thence the split beams 52 and 54 is accomplished by moving the slide 104 and by tilting the collimator holder flange 118 relative to the accessory base flange 117.

A first optical fiber 56 receives the first split beam 52, usually through a collimator, and directs the first split beam 52 against the test specimen 22 in the test specimen holder 34. In the illustrated embodiment wherein the test specimen is located within the vacuum chamber 28, there is a first-optical-fiber feedthrough 58 in the wall of the vacuum chamber 28 to pass the first optical fiber 56 into the interior of the vacuum chamber 28. The incident light beam 24 is projected from the first optical fiber 56 toward the test specimen 22.

A second optical fiber 60 receives the second split beam 54, usually through a collimator, and conducts the second split beam 54 to an instrumentation module 62, which will be discussed in greater detail subsequently.

A third optical fiber 64 receives, via either reflection as illustrated or transmission, and usually through a collimator, the light measurement signal 26 from the test specimen 22 and conducts the light measurement signal 26 to the instrumentation module 62. A third-optical-fiber feedthrough 66 passes the third optical fiber 64 from the interior of the vacuum chamber 28 to its exterior.

The optical fibers 56, 60, and 64 are most preferably optical fiber bundles, although they may be single-strand optical fibers.

The light source 42 of the optical measurement apparatus 20 further includes a first light chopper 68 positioned to intercept the light beam path of the first split beam 52 between the beam splitter 48 and the first optical fiber 56, and a second light chopper 70 positioned to intercept the light beam path of the second split beam 54 between the beam splitter 48 and the second optical fiber 60. The light choppers 68 and 70 are rotating disks having openings and slits therein, so that the light reaching the instrumentation module 62 through the optical fibers 60 and 56, 64 may be alternated in a controlled manner. The light choppers 68 and 70 are preferably rotationally driven by a common motor 72.

The instrumentation module 62 includes a monochromator 74 onto which the light beams from the second optical fiber 60 (the reference beam) and the third optical fiber 64 (the light measurement signal) are alternatively directed. The monochromator 74 serves as a narrowband filter to provide only a narrow wavelength band to a detector 76 which is also part of the instrumentation module 62. The alternating output of the detector 76 serves as the basis for the determination of the thickness of the thin film test specimen 22. A motor 78 drives the structure of the monochromator 74, for adjusting its slit width and the position of the grating to tune the wavelength.

In prior optical measurement apparatus of this type, the light source included a wideband tungsten halogen lamp light source to provide the light output. Such apparatus suffered from a poor signal-to-noise ratio and insufficient resolution bandwidth. The result was that it was difficult to monitor the thickness of the thin layers of the test specimen 22. In the present approach, a narrowband laser provides the light output beam 46 of the desired wavelength, so that all of the light output is effectively used rather than a narrow bandwidth of the light output as in the case of the tungsten halogen light source. Thickness measurements of the thin films of the test specimen 22 are therefore faster and more accurate, without changing the remainder of the apparatus.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An optical measurement apparatus operable with a test specimen, the optical measurement apparatus comprising:
    a light source comprising
        a laser having an output beam, and
        a beam splitter that splits the output beam of the laser into a first split beam and a second split beam;
    a test specimen holder that holds the test specimen therein;
    a first optical fiber that receives the first split beam and directs the first split beam against the test specimen in the test specimen holder;
    an instrumentation module;
    a second optical fiber that receives the second split beam and conducts the second split beam to the instrumentation module; and
    a third optical fiber that receives a light measurement signal from the test specimen in the test specimen holder and conducts the light measurement signal to the instrumentation module.

2. The apparatus of claim 1, wherein the laser is an infrared laser.

3. The apparatus of claim 1, wherein the light source comprises:
    a light collimator that directs the output beam to the beam splitter, and
    a source optical fiber that conducts the output beam from the laser to the light collimator.

4. The apparatus of claim 1, wherein the output beam has a diameter of at least about 2 millimeters when it is incident upon the beam splitter.

5. The apparatus of claim 1, wherein the beam splitter is a prism.

6. The apparatus of claim 1, wherein the apparatus further includes:
    a removable support upon which at least a portion of the light source is mounted.

7. The apparatus of claim 1, wherein the light source further includes
    a first light chopper positioned between the beam splitter and the first optical fiber, and
    a second light chopper positioned between the beam splitter and the second optical fiber.

8. The apparatus of claim 1, wherein the apparatus further includes
    a vacuum chamber in which the test specimen holder is contained.

9. The apparatus of claim 1, wherein the instrumentation module comprises
    a monochromator, and
    a detector.

10. The apparatus of claim 1, wherein the apparatus has as an output signal a thickness of the specimen.

11. An optical measurement apparatus operable with a test specimen, the optical measurement apparatus comprising:
    a light source comprising
        a laser having an output beam,
        a beam-splitter prism that splits the output beam of the laser into a first split beam and a second split beam,
        a light collimator that directs the output beam to the beam splitter, and
        a source optical fiber that conducts the output beam from the laser to the light collimator;
    a removable support upon which at least a portion of the light source is mounted;
    a test specimen holder that holds the test specimen therein;
    a vacuum chamber in which the test specimen holder is contained;
    a first optical fiber that receives the first split beam and directs the first split beam against the test specimen in the test specimen holder;
    an instrumentation module;
    a second optical fiber that receives the second split beam and conducts the second split beam to the instrumentation module; and
    a third optical fiber that receives a light measurement signal from the test specimen in the test specimen holder and conducts the light measurement signal to the instrumentation module.

12. The apparatus of claim 11, wherein the light source further includes
    a first light chopper positioned between the beam splitter and the first optical fiber, and
    a second light chopper positioned between the beam splitter and the second optical fiber.

13. The apparatus of claim 11, wherein the laser is an infrared laser.

14. The apparatus of claim 11, wherein the output beam has a diameter of at least about 2 millimeters when it is incident upon the beam splitter.

15. The apparatus of claim 11, wherein the beam-splitter prism and the collimator are mounted on the removable support.

16. The apparatus of claim 11, wherein the instrumentation module comprises
    a monochromator, and
    a detector.

17. The apparatus of claim 11, wherein the apparatus has as an output signal a thickness of the specimen.

18. An optical measurement apparatus operable with a test specimen, the optical measurement apparatus comprising:
- a light source that produces a monochromatic output beam which is split by a beam splitter into a monochromatic first split beam and a monochromatic second split beam;
- a test specimen holder that holds the test specimen therein;
- a vacuum chamber in which the test specimen holder is contained;
- a first optical fiber that receives the monochromatic first split beam and directs the monochromatic first split beam against the test specimen in the test specimen holder;
- an instrumentation module;
- a second optical fiber that receives the monochromatic second split beam and conducts the monochromatic second split beam from the beam splitter to the instrumentation module; and
- a third optical fiber that receives a light measurement signal from the test specimen in the test specimen holder and conducts the light measurement signal to the instrumentation module.

19. The apparatus of claim 18, wherein the light source comprises a laser producing the monochromatic output beam at 1.55 micrometers wavelength.

20. The apparatus of claim 18, wherein the apparatus has as an output signal a thickness of the specimen.

* * * * *